United States Patent
Enscore et al.

(10) Patent No.: US 12,318,492 B2
(45) Date of Patent: Jun. 3, 2025

(54) ABUSE AND MISUSE DETERRENT TRANSDERMAL SYSTEMS

(71) Applicant: Nutriband, Inc., Orlando, FL (US)

(72) Inventors: David James Enscore, Johns Creek, GA (US); Frank Tagliaferri, Decatur, GA (US); Steven Paul Damon, Johns Creek, GA (US); Alan Smith, Atlanta, GA (US); Jeffrey C. Gaulding, Peachtree Corners, GA (US)

(73) Assignee: NUTRIBAND, INC., Orlando, FL (US)

( * ) Notice: Subject to any disclaimer, the term of this patent is extended or adjusted under 35 U.S.C. 154(b) by 0 days.

(21) Appl. No.: 18/369,241

(22) Filed: Sep. 18, 2023

(65) Prior Publication Data

US 2024/0000720 A1    Jan. 4, 2024

Related U.S. Application Data (63) Continuation of application No. 17/568,999, filed on Jan. 5, 2022, now Pat. No. 11,759,431, which is a continuation of application No. 16/707,547, filed on Dec. 9, 2019, now Pat. No. 11,246,840, which is a continuation of application No. 16/190,749, filed on Nov. 14, 2018, now abandoned, which is a continuation of application No. 15/113,545, filed as application No. PCT/US2015/012196 on Jan. 21, 2015, now abandoned.

(60) Provisional application No. 62/083,620, filed on Nov. 24, 2014, provisional application No. 62/014,721, filed on Jun. 20, 2014, provisional application No. 62/014,723, filed on Jun. 20, 2014, provisional application No. 61/930,090, filed on Jan. 22, 2014, provisional application No. 61/930,104, filed on Jan. 22, 2014.

(51) Int. Cl.
| | | |
|---|---|---|
| A61K 9/70 | (2006.01) | |
| A61K 31/167 | (2006.01) | |
| A61K 31/4458 | (2006.01) | |
| A61K 31/4468 | (2006.01) | |
| A61K 31/4535 | (2006.01) | |
| A61K 31/485 | (2006.01) | |
| A61K 47/18 | (2017.01) | |

(52) U.S. Cl.
CPC .......... *A61K 9/7084* (2013.01); *A61K 31/167* (2013.01); *A61K 31/4458* (2013.01); *A61K 31/4468* (2013.01); *A61K 31/4535* (2013.01); *A61K 31/485* (2013.01); *A61K 47/18* (2013.01)

(58) Field of Classification Search
None
See application file for complete search history.

(56) References Cited

U.S. PATENT DOCUMENTS

| | | |
|---|---|---|
| 7,799,157 B2 | 9/2010 | Kato et al. |
| 2004/0109886 A1 | 6/2004 | Rigby |
| 2004/0219195 A1 | 11/2004 | Hart et al. |
| 2008/0020028 A1 | 1/2008 | Shevchuk et al. |
| 2011/0245783 A1 | 10/2011 | Stinchcomb et al. |
| 2011/0263613 A1 | 10/2011 | Hendrickson |
| 2019/0076374 A1 | 3/2019 | Enscore |

FOREIGN PATENT DOCUMENTS

| | | |
|---|---|---|
| CN | 1271280 A | 10/2000 |
| CN | 1720028 A | 1/2006 |
| CN | 1780611 A | 5/2006 |
| CN | 1909892 A | 2/2007 |
| CN | 1921814 A | 2/2007 |
| CN | 101370487 A | 2/2009 |
| CN | 102099020 A | 6/2011 |
| CN | 112741822 A | 5/2021 |
| WO | 2004098567 A2 | 11/2004 |
| WO | 2005081825 A2 | 9/2005 |
| WO | 2008024408 A2 | 2/2008 |
| WO | 2008133982 A2 | 11/2008 |
| WO | 2011106700 A1 | 9/2011 |

OTHER PUBLICATIONS

International Search Report dated Apr. 23, 2015 for International Application No. PCT/US2015/012196.
International Preliminary Report on Patentability dated Aug. 4, 2016 for corresponding International Application No. PCT/US2015/012196.
European Search Report dated Jul. 26, 2017 for corresponding EP Application No. 15740893.1.
Australian Examination Report dated Mar. 2, 2018 for corresponding AU Application No. 2015209466.
Russian Office Action dated Sep. 18, 2018 for corresponding RU Application No. 2016133853.
Japanese Office Action dated Sep. 21, 2018 for corresponding JP Application No. 2016-548240.
Mexican Office Action dated Jun. 18, 2019 for corresponding MX Application No. MX/a/2016/009493.

(Continued)

*Primary Examiner* — Robert A Wax
*Assistant Examiner* — Quanglong N Truong
(74) *Attorney, Agent, or Firm* — Barnes & Thornburg LLP (57) ABSTRACT

An abuse deterrent and misuse deterrent transdermal patch comprising aversive agents incorporated in the backing layer of the patch. The aversive agents can exhibit biphasic or sustained kinetics of release with an immediate portion released rapidly and an extended portion released in a prolonged manner when exposed to a dissolution medium. The prolonged aversive agent release provides deterrence against extraction of drug from fresh and used patches and serves to prevent accidental misuse of used patches by children. The abuse deterrent and misuse deterrent patch systems can be used for transdermal delivery of therapeutically active agents and particularly those drugs that are highly prone to abuse such as opiate and opioid analgesics and stimulants.

24 Claims, 5 Drawing Sheets

(56) References Cited

OTHER PUBLICATIONS

Russian Office Action dated Apr. 4, 2019 for corresponding RU Application No. 2016133853.
Chinese Office Action dated Jul. 26, 2019 for corresponding CN Application No. 201580015604.6.
Office Action issued for corresponding Canadian Application No. 2,937,649, dated Dec. 8, 2020.
Office Action from Canadian Application No. 2,937,649, dated Feb. 7, 2022.
Office Action issued for corresponding Chinese Application No. 202211158031.0, dated May 23, 2023.
Chinese Office Action dated May 27, 2024 for corresponding CN Application No. 202211158031.0.

ABUSE AND MISUSE DETERRENT TRANSDERMAL SYSTEMS

CROSS-REFERENCE TO RELATED APPLICATIONS

This application is a Continuation application of U.S. application Ser. No. 17/568,999, filed Jan. 5, 2022, which is a Continuation Application of U.S. application Ser. No. 16/707,547, filed Dec. 9, 2019, now U.S. Pat. No. 11,246,840; which is a Continuation Application of U.S. application Ser. No. 16/190,749, filed Nov. 14, 2018; which is a Continuation Application of U.S. application Ser. No. 15/113,545, filed Jul. 22, 2016; which is a National Stage Application of International Application No. PCT/US2015/12196, filed Jan. 21, 2015; which claims the benefit of priority from U.S. Provisional Application No. 61/930,090 filed Jan. 22, 2014; U.S. Provisional Application No. 61/930,104 filed Jan. 22, 2014; U.S. Provisional Application No. 62/014,721 filed Jun. 20, 2014; U.S. Provisional Application No. 62/014,723 filed Jun. 20, 2014; and U.S. Provisional Application No. 62/083,620 filed Nov. 24, 2014, the entirety of all of which are incorporated herein by reference.

FIELD OF THE INVENTION

The present invention is in the field of transdermal drug delivery, and more particularly transdermal systems that limit the potential for intentional abuse or accidental misuse of the system.

BACKGROUND OF THE INVENTION

Transdermal drug delivery systems for single day and multi-day delivery of therapeutic agents have been developed and marketed. Many of these systems are transdermal patches. The patches often contain a significant excess of the therapeutic agent to ensure that a therapeutically effective amount of drug is delivered to the patient over the intended dosing period. As a result, used patches can contain a substantial amount of drug even after the patch is used for the prescribed dosing period. In addition, many of these drugs are highly potent and are prone to deliberate abuse or accidental misuse that can cause severe adverse reactions if ingested by children or animals.

Accidental misuse can occur when children or animals access fresh patches, patches that fall off the skin of the wearer during treatment, and discarded used patches. Additionally, if the child or animal is being treated with the transdermal patch, they could misuse the patch via removing and chewing and/or swallowing the patch and receiving the drug in a dangerous bolus dose.

There are multiple routes of abuse of these systems reported in the literature. The primary routes are using of the patch as a platform for buccal drug delivery either through chewing or through direct buccal placement and extracting the drug from the patch for injection or buccal or oral administration.

A number of patents addressing the abuse of narcotic analgesics through incorporation of a specific antagonist to the drug in the patch formulation have been granted. While these technologies may be effective, they have significant drawbacks. Specifically, to be effective the antagonist must be specific to the drug which is feasible for narcotic analgesics and some other drugs, but not transdermally deliverable drugs in general. Moreover, the mechanism of this route of abuse deterrence requires the systemic delivery of both the narcotic and its antagonist to be effective. The agonist and antagonist must be delivered in the proper ratio and the antagonist must not be cleared from the body more rapidly than the narcotic analgesic. Exemplar patents addressing transdermal system abuse deterrence via incorporation of drug antagonists are U.S. Pat. Nos. 5,149,538, 5,236,714, and 7,182,955.

Other patents approach abuse deterrent transdermal patches from a more generic direction by incorporating aversive agents (bittering, pungent, and emetic agents) that make abuse of the patch difficult. If the aversive agents are combined with the drug in the skin contact layer of the transdermal patch, the agents must not be transdermally permeable or not cause adverse systemic effects and must not irritate the skin or exhibit their intended aversive effect when the patch is used as intended (for example, eliciting a burning sensation when a pungent agent such as capsaicin is used as the aversive agent). Therefore, much of the art discloses incorporation of the aversive agent in a location in the patch where it is not deliverable transdermally, but can manifest its deterrent effect when the patch is abused. Some of the art discloses placement of the aversive agent in or on the system backing layer distal from the drug containing layer.

The use of aversive agents incorporated in the patch backing is a general technology that can be applied to all transdermally deliverable drugs and can deter abuse of the patch in some abuse scenarios such as chewing of the patch or extraction of the aversive agent along with the drug for subsequent injection or buccal or oral administration. One such patch system is disclosed in U.S. Pat. No. 7,011,843. However, there are relatively simple means for a user to separate the drug from the aversive agent prior to abuse. One means is physical separation of the patch backing layer containing the aversive agent from the drug containing layer of the patch. Another means is placing the patch in water, alcohol, or another common solvents to elute the aversive agent from the backing layer while leaving the patch release liner in place to largely preclude elution of the drug. This would allow subsequent abuse of the patch via ingestion, buccal placement, or elution of drug from the formulation that does not contain the aversive agent for buccal or oral delivery or injection. Thus, there is still a need for transdermal systems that effectively deter misuse and intentional abuse of transdermal drug systems.

SUMMARY OF THE INVENTION

In one aspect, the invention provides an abuse deterrent or misuse deterrent transdermal patch system comprising a patch backing layer, wherein one or more aversive agents is incorporated into or irreversibly adhered onto the distal side of the patch backing layer, and wherein the one or more aversive agents exhibits a biphasic or sustained release profile when immersed in a dissolution medium.

In another aspect, the invention provides an abuse deterrent or misuse deterrent transdermal drug delivery system comprising a patch backing layer, an adhesive drug-containing layer, and a release liner, wherein one or more aversive agents is incorporated into or irreversibly adhered onto the distal side of the patch backing layer, wherein the adhesive drug-containing layer comprises one or more therapeutically active agents, wherein said adhesive drug-containing layer is adhered to the proximal side of the patch backing layer, wherein the release liner is reversibly adhered to the adhesive drug-containing layer, and wherein the release liner is a permeable release liner.

DETAILED DESCRIPTION OF THE INVENTION

Figure 1A:
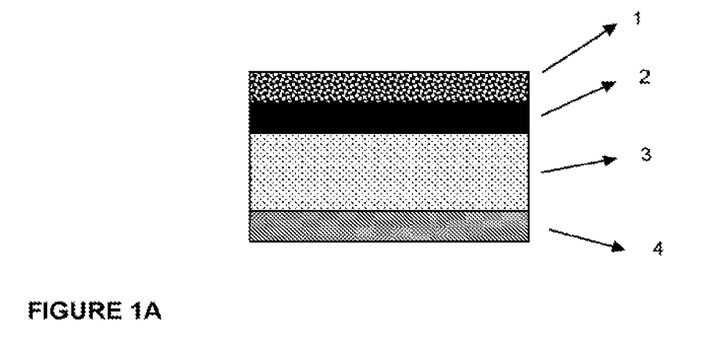
FIG. 1A is a cross-sectional view of an abuse deterrent/misuse deterrent patch system in accordance with the present invention.
Figure 1B:
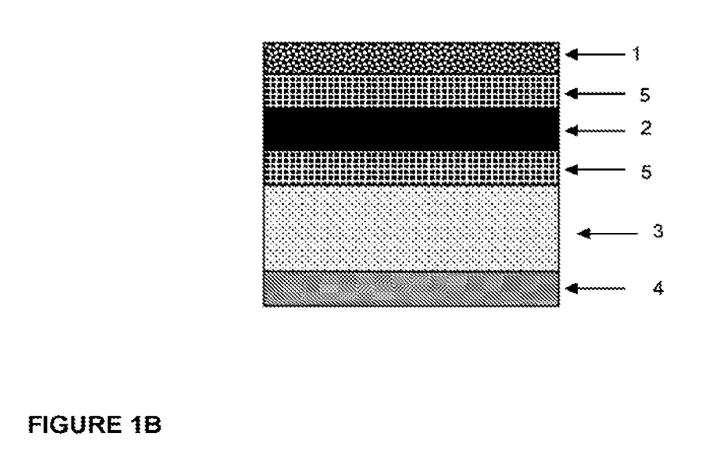
FIG. 1B is a cross-sectional view of another abuse deterrent/misuse deterrent patch system in accordance with the present invention.

The present invention provides an abuse deterrent or misuse deterrent patch system. The patch system can be a transdermal drug delivery patch system or an overlay patch system for deterring misuse. FIG. 1 illustrates an abuse deterrent or misuse deterrent patch system in accordance with a particular embodiment of the invention. Aversive agent layer 1 is irreversibly adhered to the distal side of patch backing layer 2. Adhesive layer or adhesive drug-containing layer 3 is irreversibly adhered to the proximal side of backing layer 2. Release liner 4 is reversibly adhered to adhesive layer or adhesive drug-containing layer 3.

The abuse deterrent or misuse deterrent transdermal system of this invention utilizes an aversive agent or combination of aversive agents. As used herein, the term "aversive agent" means any agent that elicits a strong, temporary, non-lethal negative reaction in an animal, including humans, that is exposed to the agent. Such aversive agents include, but are not limited to, bittering agents, pungent agents, and emetic agents. In one embodiment, the aversive agents are agents that act locally rather than requiring systemic absorption by the animal exposed to the agent. Locally active agents elicit a negative sensation (e.g. foul taste, burning sensation or emesis) when placed in the mouth or elicit a burning sensation or other negative sensation when inhaled, injected, or placed rectally or vaginally. Suitable aversive agents include but are not limited to denatonium benzoate, denatonium saccharide, sucrose octaacetate, quercetin, capsaicin, resiniferatoxin, quassin, brucine, piperine, allyl isothiocyanate, alum, copper sulfate, and emetine. In some embodiments, the aversive agent is selected to have some permeability across intact human skin. In some embodiments, two or more aversive agents are incorporated to increase the deterrence or to deter multiple methods of abuse or misuse.

As used herein, the phrase "therapeutically active agent" means any prescription, over-the-counter, or compounded pharmaceutical or medicinal agent, including vitamins, mineral supplements and natural products, that elicits a physiological response in an animal following administration of the agent and generally intended to treat or prevent an injury or illness. The phrase "therapeutically active agent" and the term "drug" are used interchangeably herein.

The transdermal patch systems in accordance with the present invention comprise a backing layer. The backing layer is typically made of a material or combination of materials that is impermeable or at least substantially impermeable to the aversive agent(s) and the therapeutically active agent(s), if present. The backing layer can be a single layer or multiple layers of the same or different materials. Materials for preparing backing layers for transdermal patch systems are well known in the art. Suitable materials for the backing layer include polyolefins, including polyethylene and polypropylene; polyesters, including polyethylene terephthalate, multi-layer EVA film and polyester; polyurethane; or a combination thereof. Other suitable materials include, but are not limited to, cellulose acetate, plasticized vinyl acetate-vinyl chloride copolymers, nylon, polyvinylidene chloride (e.g. SARAN), ethylene-methacrylate copolymerer (Surlyn), aluminum foil and polymer-metal composites.

The backing layer may be flexible or non-flexible. In one embodiment, the backing layer is flexible and can conform to the shape of the body member of the animal to which the transdermal patch system is adhered.

The backing layer in accordance with the present invention has a distal side and a proximal side. The aversive agent(s) is incorporated into or onto the distal side of the backing layer of the transdermal patch. The adhesive layer, with or without a therapeutically active agent, that comes into contact with the skin of the animal that is wearing the patch is on the proximal side of the backing layer. Positioning the aversive agent(s) on the distal side of the impermeable backing layer prevents delivery of the aversive agent(s) to the proximal side of the patch. Positioning the therapeutically active agent on the proximal side of the impermeable backing layer prevents delivery of the therapeutically active agent to the distal side of the backing layer.

The aversive agent(s) can be bonded to the distal side of the backing layer alone or can be dissolved, dispersed, or dissolved and dispersed in one or more polymer film layers that is applied to the backing layer. Preferred polymer layers adhere strongly to the backing layer but are non-adhesive to prevent the aversive agent layer from sticking to clothing or fur.

Figure 2:
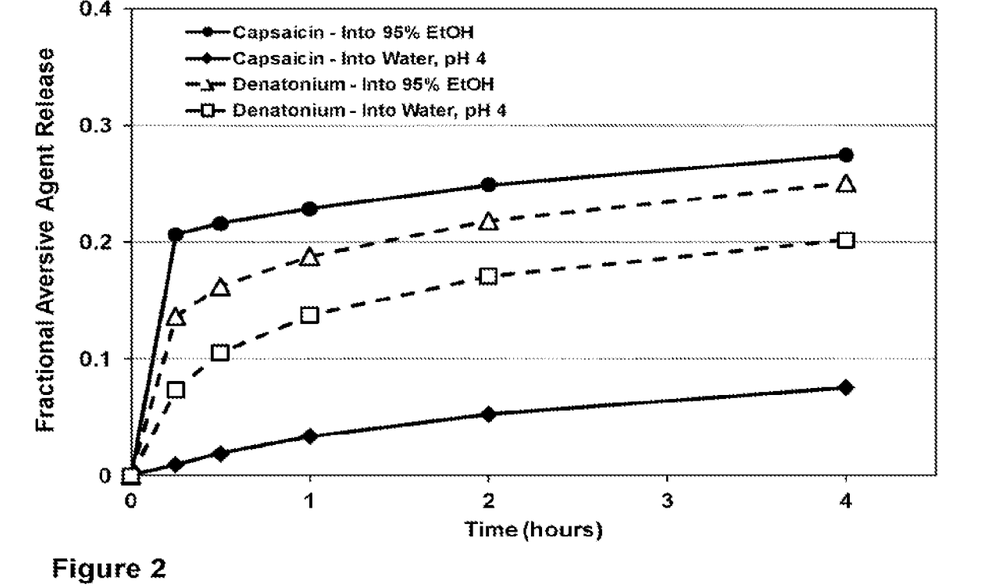
FIG. 2 is a representative graph of fractional release of aversive agents into water or 95% ethanol over time.

In some embodiments, the backing layer has an extended surface area or additional layer, such as foam or woven or non-woven fabric, irreversibly bonded to one or both sides of the drug impermeable backing layer. The extended surface can function as an anchor for the aversive agent layer, the adhesive drug-containing layer, or both and serve to increase the difficulty of physical separation of the patch layers from each other. FIG. 1A illustrates an abuse deterrent or misuse deterrent patch system in accordance with this particular embodiment of the invention. Aversive agent layer 1 is irreversibly adhered to the distal side of patch backing 2 via a non-woven fabric or foam layer 5. Adhesive layer or adhesive drug-containing layer 3 is irreversibly adhered to the proximal side of backing layer 2 via a non-woven fabric or foam layer 5. Release liner 4 is reversibly adhered to adhesive layer or adhesive drug-containing layer 3. In FIG. 2, both the proximal and distal sides of the impermeable backing layer 2 have a bonded layer of non-woven fabric 5. However, in certain embodiments, non-woven fabric layer 5 is present only on the distal side or only on the proximal side of backing layer 2.

The aversive agent(s) can be incorporated into one or more polymers to form a thin film. Suitable polymers for preparing such layers include, without limitation, polyisobutylene, styrene-isoprene-styrene copolymer, natural rubber, ethylene/vinyl acetate copolymers (5-percent vinyl acetate), polyethylene, ethylene/ethyl acrylate copolymers (5-60 percent ethyl acrylate), polyvinyl pyrrolidone and crosslinked polyvinyl pyrrolidone, and cellulosic polymers. As used herein, the phrase "polymer layer" means one or more polymeric thin film layers. The individual film layers can be laminated after extrusion, can be solvent cast onto the backing layer or can be co-extruded. Manufacture of such single and multi-film layers are well known in the art. The polymer layer containing the aversive agent may contain highly water soluble agents such as simple salts or polyvinyl pyrrolidone to promote rapid initial release of the aversive agent(s) when the polymer layer contacts a dissolution medium.

As used herein, the phrase "dissolution medium" means an aqueous or non-aqueous liquid solvent. Aqueous liquid solvents include, without limitation, those liquids comprising only water, solutions comprising water and one or more salts, acids or bases, or solutions comprising water and one or more alcohols such as ethanol or isopropanol. Non-aqueous liquid solvents include, without limitation, those liquids other than water and water solutions, including, but not limited to, common household solvents such as ethanol, isopropyl alcohol, acetone, ethyl acetate, toluene, and mineral spirits. The skilled artisan understands that certain non-aqueous liquid solvents can comprise some amount of water, such as 95% ethanol which contains approximately 5% water. Accordingly, for purposes of the present invention, those solvents that display non-aqueous properties such as 95% ethanol are considered non-aqueous, whereas solutions such as 50% ethanol and 50% water that display aqueous properties are generally considered aqueous solvents.

In certain embodiments, the aversive agent(s) are released in a biphasic or sustained release profile when immersed in a dissolution medium. The biphasic or sustained release profile consists of an immediate release phase and an extended release phase. The immediate release phase is the phase in which a portion of the aversive agent(s) releases from the backing layer immediately or very shortly after contacting a dissolution medium or moisture in one or more body cavities such as the mouth, nose, rectum or vagina, without the need for chewing or other grinding or abrasion of the patch. In one embodiment of the present invention, the immediate release portion of the aversive agent(s) is an amount sufficient to elicit the aversive effect prior to an overdose or potentially toxic dose of the drug being released from the patch. For example, if a pungent aversive agent is used and the system is placed in the mouth, the immediate release portion of the aversive agent(s) is an amount sufficient to produce a burning sensation that compels the animal being exposed to remove the patch from its mouth before an overdose or potentially toxic quantity of the drug is released.

The extended portion of the aversive agent(s) is incorporated into the polymer layer in a manner to be released more slowly than the immediate portion. In one embodiment of the present invention, the extended release portion is the portion of aversive agent that is released over a sufficiently long period of time such that a large quantity of the drug in the patch would be extracted into a dissolution medium during the same period of time as the aversive agent, with or without the patch release liner being left in place. The extended release portion renders it more difficult to effectively separate the drug and aversive agent(s) through sequential extraction. In addition, the extended release portion of the aversive agent(s) can provide for an effective amount of the aversive agent in used patches even if the patch is worn during bathing or swimming.

The biphasic or sustained pattern of the aversive agent(s) release can be achieved via several mechanisms. In one embodiment, the aversive agent can be incorporated into a matrix polymer that has low diffusivity and solubility for the aversive agents and is not plasticized by the dissolution medium. Suitable matrix polymers include, but are not limited to, polyisobutylene. In another embodiment, the release pattern of the aversive agent from the matrix polymer can be modified by incorporating multiple layers of the matrix polymer or layers of the same or different matrix polymers comprising different concentrations of the aversive agents. In other embodiments, biphasic or sustained release patterns can be achieved via microencapsulation of the extended release portion of the aversive agent(s) prior to incorporation of the agent(s) into the polymer layer. Encapsulating polymers know in the drug delivery art can be used to create the aversive agent(s) microcapsules. Such polymers include, without limitation, polylactic acid, lactic acid/glycolic acid copolymers, polyvinyl alcohol, acrylic and methacrylic polymers, and cellulosic polymers. Other methods of extending the release of the extended release portion of the aversive agent(s) include positioning the agent(s) behind a discrete controlling membrane layer within the polymer layer and reversibly bonding the agents to the chains of the polymer layer are also in accordance with the invention. The rate controlling membrane can be either dense or microporous and selected, without limitation, from ethylene/vinyl acetate copolymers (5-60 percent vinyl acetate), polyethylene, ethylene/ethyl acrylate copolymers (5-60 percent ethyl acrylate), polyethylene, polypropylene, and cellulosic polymers.

Transdermal patch systems generally include a release liner. The release liner is reversibly adhered to the adhesive layer and is removed to expose the adhesive to allow the user to adhere the patch to the skin. Release liners for transdermal patches are typically a film composed of a glassy polymer, such as polyethylene terephthalate, coated with a silicone or fluorocarbon release coating. The liners are typically impermeable to the drug contained in the patch and are unaffected by immersion into water or other liquid media. In one embodiment of the invention, the release liner functions identically to the liners described above when dry, but the liner of the present invention becomes highly permeable to the drug contained in the patch when immersed in a dissolution medium. Such liner is hereinafter referred to as a "permeable release liner." Suitable materials for the permeable release liner include, but are not limited to, hydratable cellulose and starch-impregnated Kraft paper coated with a silicone or fluorocarbon release coating. The dissolution medium may be of acidic, basic, or neutral pH and can include pure water.

In another embodiment, the liner is a perforated permeable release liner. The perforated permeable release liner is a permeable release liner that is perforated with an array of holes to render the liner highly permeable to drug when the patch is submersed in a dissolution medium that is non-aqueous, in addition to becoming permeable to the drug in the patch when the liner is submersed into an aqueous dissolution medium. In one embodiment, the holes in the perforated permeable release liner are from about 0.05 to about 0.50 mm in diameter. In another embodiment, the holes are from about 0.2 to about 0.4 mm in diameter. In certain embodiments, the holes are relatively uniformly dispersed at a density of from about 75 to 150 holes per square centimeter. In another embodiment, the holes are relatively uniformly dispersed at a density of from about 100 to 150 holes per square centimeter. Without being restricted by any particular theory, the perforations alone may be sufficient for drug penetration through the liner into non-aqueous liquid media but not sufficient for drug penetration through the liner in many aqueous liquid media due to the high surface tension of water. A liner that becomes highly drug permeable when exposed to an aqueous liquid medium, or a similar permeable release liner that is perforated and also becomes highly drug permeable when exposed to non-aqueous liquid media due to the perforations, limits the potential abuser from effectively serially eluting the aversive agent(s) followed by the therapeutically active agent without aversive agent. Those skilled in the art understand that not all drugs and all aversive agents will elute in similar time frames into the same solvent. Thus, in certain embodiments, the aversive agents and the drug(s) will have similar solubility characteristics.

The backing layer containing the aversive agent(s) that releases in a biphasic or sustained pattern, the release liner that becomes drug permeable when placed in a dissolution medium, and the perforated release liner that becomes drug permeable when placed in a dissolution medium can be used with any type of transdermal patch with an adhesive drug-containing layer. The adhesive drug-containing layer can be a single drug in adhesive layer, a multilayer drug releasing system or a drug reservoir system. Suitable adhesive drug-containing transdermal patches in accordance with the present invention include, without limitation, drug in adhesive (matrix) patches, multilaminate patches with or without rate control membranes, and liquid reservoir patches. In one embodiment, the patch system is a matrix patch. In another embodiment, the patch system is a multilaminate patch. In another embodiment, the patch system is a liquid reservoir patch. Patch systems such as those previously mentioned are well known in the art. See, for example, Transdermal and Topical Drug Delivery Systems, Ghosh, Pfister, and Yum editors, Interpharm Press, 1997.

The abuse deterrent and misuse deterrent systems of the present invention can be used with transdermal patches containing any therapeutically active agent suitable for transdermal delivery. In certain embodiments, the patches contain therapeutically active agents that have a known history of abuse such as, without limitation, opioid and opiate analgesics including fentanyl, sufentantil, and buprenorphine, and stimulant drugs such as methylphenidate. In other embodiments, the abuse deterrent and misuse deterrent systems can be used to minimize misuse or accidental use of adhesive drug-containing patches by children or caregivers. Such patches may contain non-opiate analgesics such as lidocaine, diclofenac or glucocorticoids, or sex steroid hormones such as progesterone, estrogen or testosterone.

In some embodiments of the present invention, the abuse deterrent and misuse deterrent aversive agent-containing polymer layers can be used in adhesive patches that do not contain any therapeutically active agent but instead are intended to be applied over another transdermal drug delivery system or over an area of injury or treatment on an animal. Such systems can be used to deter a non-human animal or a child from licking or chewing on the applied patch or the area of treatment or injury. The aversive agent backing can be incorporated onto a backing layer in a similar fashion as described above for a patch system containing a drug. The aversive agents can be released immediately, over time, or in a sustained release or biphasic pattern. Thus, in one embodiment, the present invention provides an abuse deterrent or misuse deterrent transdermal patch system comprising an adhesive layer, wherein the adhesive layer and the entire patch system is free or essentially free of any drug.

The following examples are merely illustrative of certain embodiments of the present invention and should not be considered as limiting the scope of the invention in any way. These examples and equivalents thereof will become more apparent to those skilled in the art in light of the present disclosure and the accompanying claims.

EXAMPLES

Example 1. An abuse deterrent system backing for a transdermal patch is prepared using a commercial backing comprising a 50 micrometer polyethylene terephthalate film bound to an ethylene/vinyl acetate film containing dissolved and dispersed aversive agents and aversive agents in dispersed poly(DL-lactide-co-glycolide) microparticles. A mixture of denatonium benzoate (1 weight percent), capsaicin (3 weight percent), and polyvinyl pyrrolidone (3 weight percent; K value 30) are added to ethylene/vinyl acetate copolymer (40 percent VA). The mixture is heated and agitated in the mixing chamber of a kneader extruder until uniform. A 1:3 blend of denatonium benzoate and capsaicin totaling weight percent on a dry basis is dissolved in a 10 weight percent solution of poly(DL-lactide-co-glycolide) in methylene chloride. Microparticles of the aversive agents and PLGA are manufactured via spray drying or oil-in-water emulsion/evaporation and the particles are added at a 20 weight percent loading to the heated blend of aversive agents, polyvinylpyrrolidone and ethylene/vinyl acetate copolymer, and the mix is agitated until uniform. A 25 micrometer thick film of the heated polymer layer is extruded onto one side of the polyethylene terephthalate film.

A standard formulation of fentanyl in acrylic adhesive solution used in common subsaturated fentanyl transdermal patches is cast on the other side of the polyethylene terephthalate backing and allowed to dry. A 2 mil thick siliconized polyethylene terephthalate release liner is laminated to the dried adhesive. Finished abuse deterrent transdermal fentanyl patches are die cut to the appropriate area and pouched.

Example 2. An abuse deterrent system backing for a transdermal patch is prepared using a commercial backing comprising a 50 micrometer polyethylene terephthalate film bound to an ethylene/vinyl acetate film containing dissolved and dispersed aversive agent and aversive agent in dispersed poly DL-lactide microparticles. A mixture of capsaicin (5 weight percent), and polyvinyl pyrrolidone (3 weight percent; K value 30) are added to ethylene/vinyl acetate copolymer (40 percent VA). The mixture is heated and agitated in the mixing chamber of a kneader extruder until uniform. Capsaicin (10 weight percent) is dissolved in a 10 weight percent solution of poly DL-lactide in methylene chloride. Microparticles of capsaicin and poly DL-lactide are manufactured via spray drying or oil-in-water emulsion/evaporation and the particles are added at a 20 weight percent loading to the heated blend of aversive agent, polyvinylpyrrolidone and ethylene/vinyl acetate copolymer and the mix is agitated until uniform. A 25 micrometer thick film of the heated polymer layer is extruded onto one side of the polyethylene terephthalate film.

A standard formulation of fentanyl in acrylic adhesive solution used in common subsaturated fentanyl transdermal patches is cast on the other side of the polyethylene terephthalate backing and allowed to dry. A 2 mil thick siliconized polyethylene terephthalate release liner is laminated to the dried adhesive. Finished abuse deterrent transdermal fentanyl patches are die cut to the appropriate area and pouched.

Example 3. An abuse deterrent system backing for a transdermal patch is prepared using a commercial backing comprising a layer of non-woven polyester adhesively laminated to a layer of dense polyethylene terephthalate film. 2 weight percent denatonium benzoate and 5 weight percent capsaicin and 5 weight percent polyvinyl pyrrolidone (K value 30) are added (on a solids basis) to a 40 weight percent solution of ethylene/vinyl acetate copolymer (40 percent VA) dissolved in methylene chloride. The mixture is agitated until uniform and then cast into a film on the non-woven side of the commercial backing material and allowed to dry.

A standard formulation of fentanyl in acrylic adhesive solution used in common subsaturated fentanyl transdermal patches is cast on the dense polyethylene terephthalate film side of the backing and allowed to dry. A 2 mil thick film of hydratable cellulose coated with a silicone release coating is laminated to the dried adhesive fentanyl containing layer. Finished abuse deterrent transdermal fentanyl patches are die cut to the appropriate area and pouched.

Example 4. A transdermal patch is prepared as in Example 3 except that the 2 mil thick film of hydratable cellulose coated with a silicone release coating is replaced with a 3 mil thick film of hydratable cellulose coated with a silicone release coating perforated with an array of 0.3 mm diameter holes at a density of 125 holes per square centimeter. The perforated release liner is laminated to the dried adhesive layer containing fentanyl. Finished abuse deterrent transdermal fentanyl patches are die cut to the appropriate area and pouched.

Example 5. A misuse deterrent system backing for a transdermal patch is prepared using a commercial backing comprising a 50 micrometer polyethylene terephthalate film bound to an ethylene/vinyl acetate film containing dissolved and dispersed aversive agents and aversive agents in dispersed poly(DL-lactide-co-glycolide) microparticles. A mixture of denatonium benzoate (1 weight percent), capsaicin (3 weight percent), and polyvinyl pyrrolidone (3 weight percent; K value 30) are added to ethylene/vinyl acetate copolymer (40 percent VA). The mixture is heated and agitated in the mixing chamber of a kneader extruder until uniform. A 1:3 blend of denatonium benzoate and capsaicin totaling 10 weight percent on a dry basis is dissolved in a 10 weight percent solution of a starch in water at a temperature above 80° C. Microparticles of the aversive agents and starch are manufactured via spray drying and the particles are added at a 20 weight percent loading to the heated blend of aversive agents, polyvinylpyrrolidone and ethylene/vinyl acetate copolymer and the mix is agitated until uniform. A 25 micrometer thick film of the heated polymer layer is extruded onto one side of the polyethylene terephthalate film.

A standard formulation of fentanyl in acrylic adhesive solution used in common subsaturated fentanyl transdermal patches is cast on the dense polyethylene terephthalate film side of the backing and allowed to dry. A 2 mil thick film of hydratable cellulose coated with a silicone release coating is laminated to the dried adhesive fentanyl containing layer. Finished abuse deterrent transdermal fentanyl patches are die cut to the appropriate area and pouched.

Example 6. A misuse deterrent overlay patch is prepared as is the abuse deterrent backing in Example 1 except that a 50 micrometer (dry thickness) film of a commercially available acrylate adhesive containing no drug, instead of the fentanyl dissolved in acrylic adhesive of Example 1, is cast. A siliconized polyester release liner is then laminated to the dried adhesive.

Example 7. A misuse deterrent overlay patch is prepared using a commercial backing comprising a 12 micrometer polyethylene terephthalate film bound to an ethylene/vinyl acetate film containing dissolved and dispersed aversive agent and aversive agent. A mixture of capsaicin (5 weight percent), and polyvinyl pyrrolidone (3 weight percent; K value 30) are added to ethylene vinyl acetate copolymer (40 percent VA). The mixture is heated and agitated in the mixing chamber of a kneader extruder until uniform. Capsaicin (10 weight percent) is mixed with the ethylene/vinyl acetate copolymer and a 25 micrometer thick film of the heated polymer layer is extruded onto one side of the polyethylene terephthalate film. A 50 micrometer (dry thickness) film of a commercially available acrylate adhesive is cast on the side of the overlay backing opposite the side containing the aversive agents and allowed to dry. A siliconized polyester release liner is then laminated to the dried adhesive.

Example 8. A misuse deterrent overlay patch is prepared as is the abuse deterrent backing in Example 5 except that a 50 micrometer (dry thickness) film of a commercially available acrylate adhesive containing no drug, instead of the fentanyl dissolved in acrylic adhesive of Example 5, is cast. A siliconized polyester release liner is then laminated to the dried adhesive.

Example 9. A misuse deterrent system backing for a transdermal patch is prepared using a commercial backing for transdermal patches containing 3 layers, ethylene/vinyl acetate copolymer, polyethylene terephthalate, and medium density polyethylene (Scotchpak 9730, 3M). Polyisobutylene (MW 1,000,000, BASF) was dissolved in n-heptane (Fisher Scientific) and the solids content determined. An approximate 2 mL volume of the polyisobutylene solution was weighed into a glass scintillation vial and the mass of polymer calculated. The mass of denatonium benzoate (Alfa Aesar) and capsaicin (Chem-Impex, Intl) to result in a 15 weight percent loading of each agent in the polyisobutylene on a dry basis was calculated. These masses of the aversive agents were weighed into a separate scintillation vial and dissolved in a small volume of methylene chloride (Spectrum). The aversive agent methylene chloride solution was added to the vial containing the polyisobutylene solution and the mixture was vortexed until a visually uniform dispersion was formed. The solution containing the polyisobutylene and aversive agents was cast onto the medium density polyethylene side of the backing film using a casting knife and the resulting film was dried in a convection oven at 80° C.

A standard formulation of fentanyl in acrylic adhesive solution used in common subsaturated fentanyl transdermal patches is cast on the dense polyethylene terephthalate film side of the backing and allowed to dry. A 2 mil thick film of hydratable cellulose coated with a silicone release coating is laminated to the dried adhesive fentanyl containing layer. Finished abuse deterrent transdermal fentanyl patches are die cut to the appropriate area and pouched.

Example 10. A misuse deterrent system backing for a transdermal patch with two layers of aversive agent matrix is prepared using a commercial backing for transdermal patches containing 3 layers, ethylene/vinyl acetate copolymer, polyethylene terephthalate, and medium density polyethylene (Scotchpak 9730, 3M). The first aversive agent layer was prepared as follows. Polyisobutylene (MW 1,000,000, BASF) was dissolved in n-heptane (Fisher Scientific) and the solids content determined. An approximate 2 mL volume of the polyisobutylene solution was weighed into a glass scintillation vial and the mass of polymer calculated. The mass of denatonium benzoate (Alfa Aesar) and capsaicin (Chem-Impex, Intl) to result in a 15 weight percent loading of each agent in the polyisobutylene on a dry basis was calculated. These masses of the aversive agents were weighed into a separate scintillation vial and dissolved in a small volume of methylene chloride (Spectrum). The aversive agent methylene chloride solution was added to the vial containing the polyisobutylene solution and the mixture was vortexed until a visually uniform dispersion was formed. The solution containing the polyisobutylene and aversive agents was cast onto the medium density polyethylene side of the backing film using a casting knife and the resulting film was dried in a convection oven at 80° C. The second aversive agent layer was prepared as follows. Polyisobutylene (MW 1,000,000) was dissolved in n-heptane and the solids content determined. An approximate 2 mL volume of the polyisobutylene solution was weighed into a glass scintillation vial and the mass of polymer calculated. The mass of denatonium benzoate and capsaicin to result in a 5 weight percent loading of each agent in the polyisobutylene on a dry basis was calculated. These masses of the aversive agents were weighed into a separate scintillation vial and dissolved in a small volume of methylene chloride (Spectrum). The aversive agent methylene chloride solution was added to the vial containing the polyisobutylene solution and the mixture was vortexed until a visually uniform dispersion was formed. The solution containing the polyisobutylene and aversive agents was cast over the first layer using a casting knife and the resulting bilayer film was dried in a convection oven at 80° C.

A standard formulation of fentanyl in acrylic adhesive solution used in common subsaturated fentanyl transdermal patches is cast on the dense polyethylene terephthalate film side of the backing and allowed to dry. A 2 mil thick film of hydratable cellulose coated with a silicone release coating is laminated to the dried adhesive fentanyl containing layer. Finished abuse deterrent transdermal fentanyl patches are die cut to the appropriate area and pouched.

Example 11. A misuse deterrent overlay patch is prepared as is the abuse deterrent backing in Example 9 except that a 50 micrometer (dry thickness) film of a commercially available acrylate adhesive containing no drug, instead of the fentanyl dissolved in acrylic adhesive of Example 5, A siliconized polyester release liner is then laminated to the dried adhesive.

Example 12. An aversive agent backing layer was prepared to determine the release patterns of two aversive agents. Polyisobutylene (MW 1,000,000, BASF) was dissolved in n-heptane (Fisher Scientific) and the solids content determined. An approximate 2 mL volume of the polyisobutylene solution was weighed into a glass scintillation vial and the mass of polymer calculated. The mass of denatonium benzoate (Alfa Aesar) and capsaicin (Chem-Impex, Intl) to result in a 15 weight percent loading of each agent in the polyisobutylene on a dry basis was calculated. These masses of the agents were weighed into a separate scintillation vial and dissolved in a small volume of methylene chloride (Spectrum). The aversive agent methylene chloride solution was added to the vial containing the polyisobutylene solution and the mixture was vortexed until a visually uniform dispersion was formed. The solution containing the polyisobutylene and aversive agents was cast onto the pigmented polyethylene side of the backing film (Scotchpak 9730, 3M) using a casting knife and the resulting film was dried in a convection oven at 80° C.

Circular samples of the coated backing were cut using an arch punch and tested for aversive agent release kinetics into acidified water (pH 4) and 95% ethanol at 32° C. using a USP Apparatus 7 (Agilent Technologies). Capsaicin and denatonium were quantitated by HPLC and the fractional amount of each agent released was calculated. The results are shown in FIG. 2, wherein an immediate release portion of aversive agent is released within the first 15 minutes and an extended release portion of aversive agent is released for at least four hours.

Example 13. Lidocaine patches were prepared by dissolving polyisobutylene (1,000,000 MW, BASF) and polyisobutylene (30,000 MW, BASF) in n-heptane in a 1.25:1.0 ratio and adding 50 weight percent light mineral oil (Sonneborn) on a solids basis. 10 weight percent lidocaine base (ICN Biomedicals) was added to the PIB/MO solution (dry basis) and allowed to dissolve. The solution was mixed on a roller mill until uniform. Films were cast and the solvent dried in a convection oven at 80° C.

Figure 3:
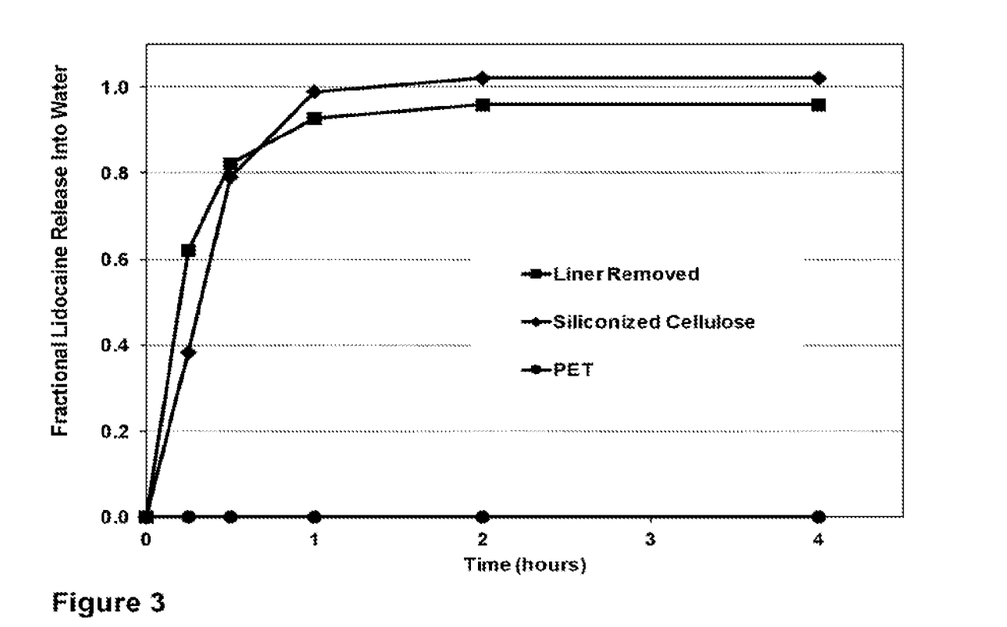
FIG. 3 is a representative graph of fractional release of lidocaine into water over time in the presence or absence of various release liners.
Figure 4:
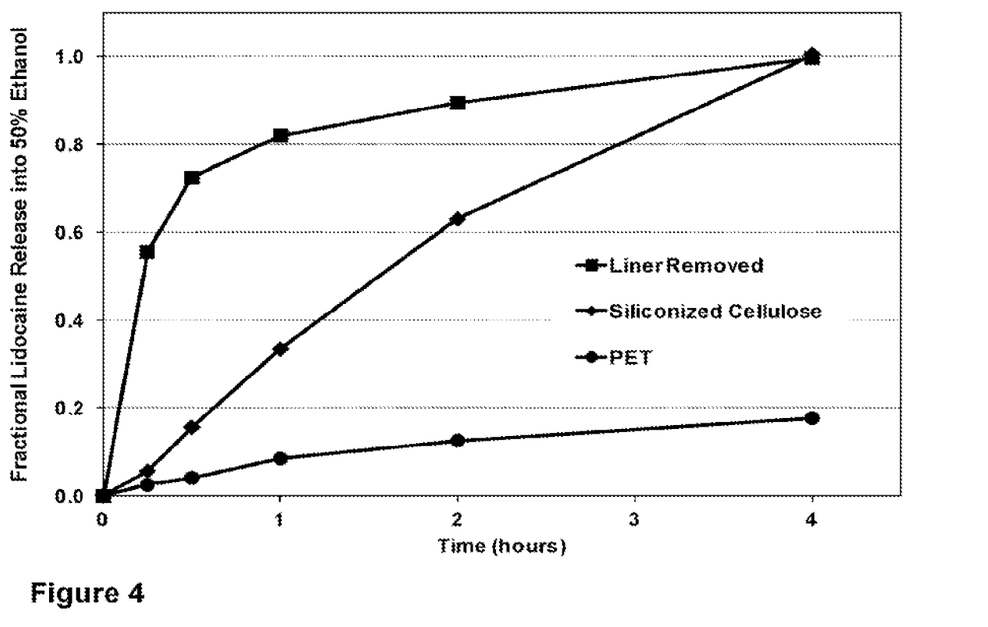
FIG. 4 is a representative graph of fractional release of lidocaine into 50% ethanol over time in the presence or absence of various release liners.

Siliconized PET, siliconized cellulose, perforated siliconized cellulose or perforated siliconized PET release liners were laminated to the dried lidocaine film. The perforated liners were prepared by passing an 8 needle×24 row (192 needles) DermaRoller (ZGTS, Jiatailonghe (Beijing) Technologies) across the siliconized cellulose or PET liner. The perforated liners had an array of 0.3 mm diameter holes with an approximate density of 125 holes per square centimeter. For all liner configurations, 18 mm diameter test patches were cut using an arch punch for release testing. Patches for each liner configuration were tested for drug release into acidified water (pH 4), 50% ethanol in water, and 95% ethanol in water using a USP Apparatus 7 (Agilent Technologies). Lidocaine was quantitated using HPLC and the fractional amount of lidocaine released was calculated. Results for lidocaine patches into water and lidocaine into 50% ethanol are shown in FIG. 3 and FIG. 4, respectively. Perforated siliconized cellulose was not tested for release into water since non-perforated siliconized cellulose provides similar results to no liner in water. Perforated siliconized cellulose and perforated PET liners into 50% ethanol were also not tested.

Example 14. Commercial fentanyl transdermal systems containing 0.41 mg of fentanyl base per square centimeter (Mylan) were tested for the kinetics of drug release at 32° C. for five release liner configurations. The commercial patch was tested without the commercially supplied liner or with the supplied PET liner. For the remaining three configurations, the commercially supplied PET liner was removed and replaced with a siliconized cellulose, perforated siliconized cellulose, or perforated siliconized PET liner. The perforated liners were prepared by passing an 8 needle×24 row (192 needles) DermaRoller (ZGTS, Jiatailonghe (Beijing) Technologies) across the commercially supplied PET liner. The perforated liners had an array of 0.3 mm diameter holes with an approximate density of 125 holes per square centimeter. For all liner configurations, 18 mm diameter test patches were cut using an arch punch for drug release testing.

Figure 5:
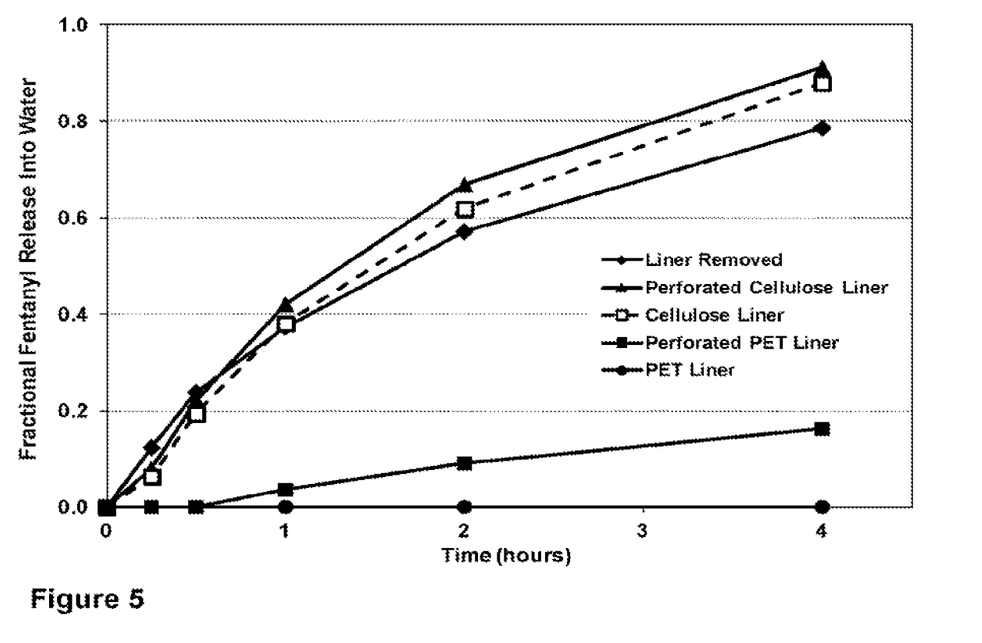
FIG. 5 is a representative graph of fractional release of fentanyl into water over time in the presence or absence of various release liners.
Figure 6:
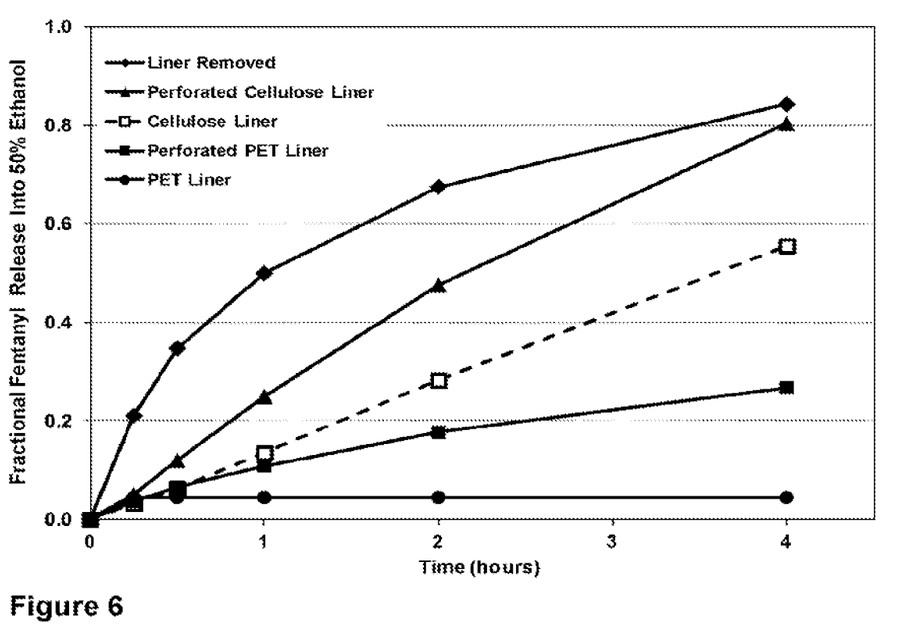
FIG. 6 is a representative graph of fractional release of fentanyl into 50% ethanol over time in the presence or absence of various release liners.
Figure 7:
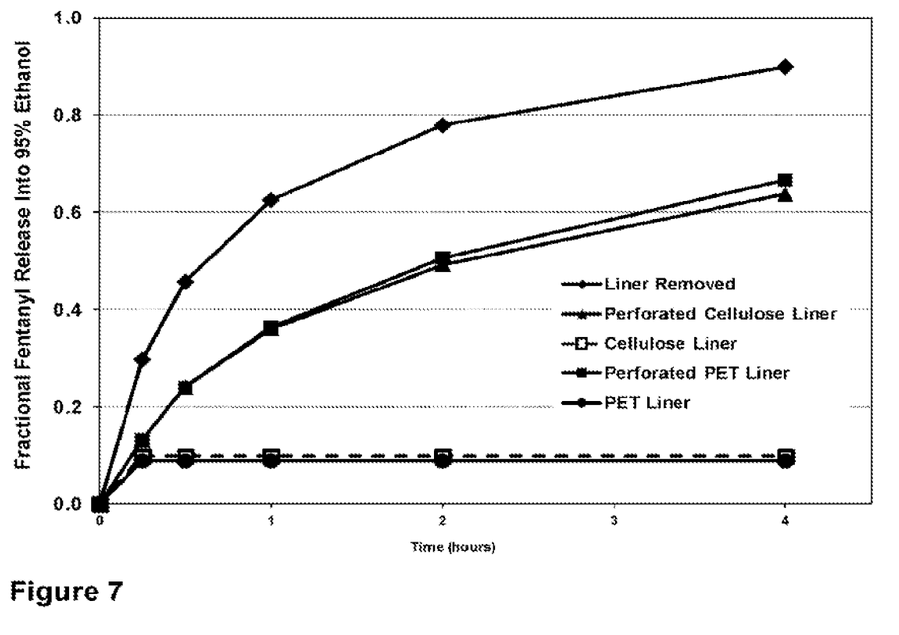
FIG. 7 is a representative graph of fractional release of fentanyl into 95% ethanol over time in the presence or absence of various release liners.

Patches for each liner configuration were tested for drug release into acidified water (pH 4), 50% ethanol in water, and 95% ethanol in water using a USP Apparatus 7 (Agilent Technologies). Fentanyl was quantitated using HPLC and the fractional amount of fentanyl released was calculated. Results for fentanyl released into water, 50% ethanol and 95% ethanol for each liner configuration are shown in FIG. 5, FIG. 6 and FIG. 7, respectively.

Figure 8:
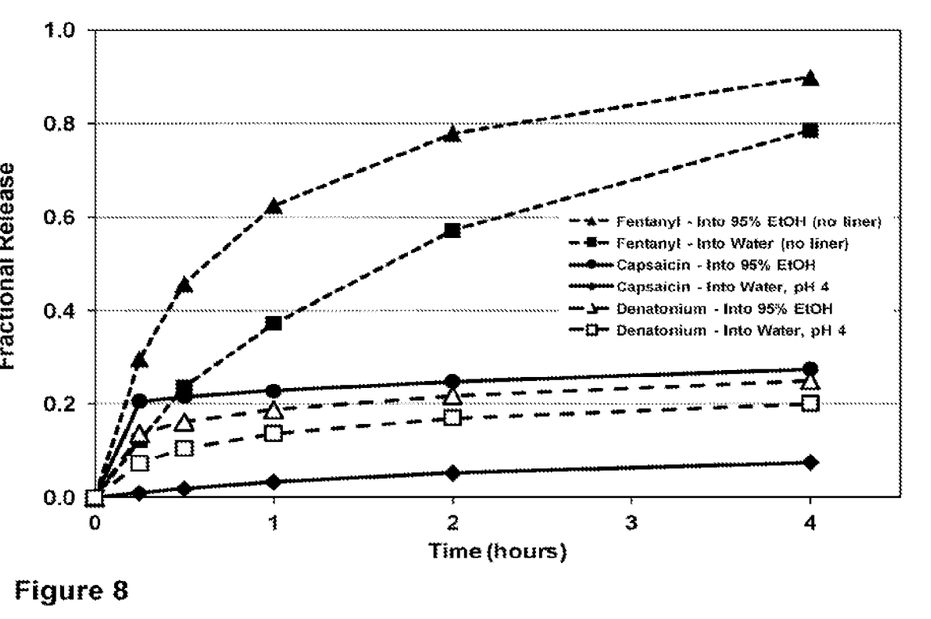
FIG. 8 is a representative graph of fractional release of aversive agents and fentanyl into water or 95% ethanol over time in the absence of release liners.
Figure 9:
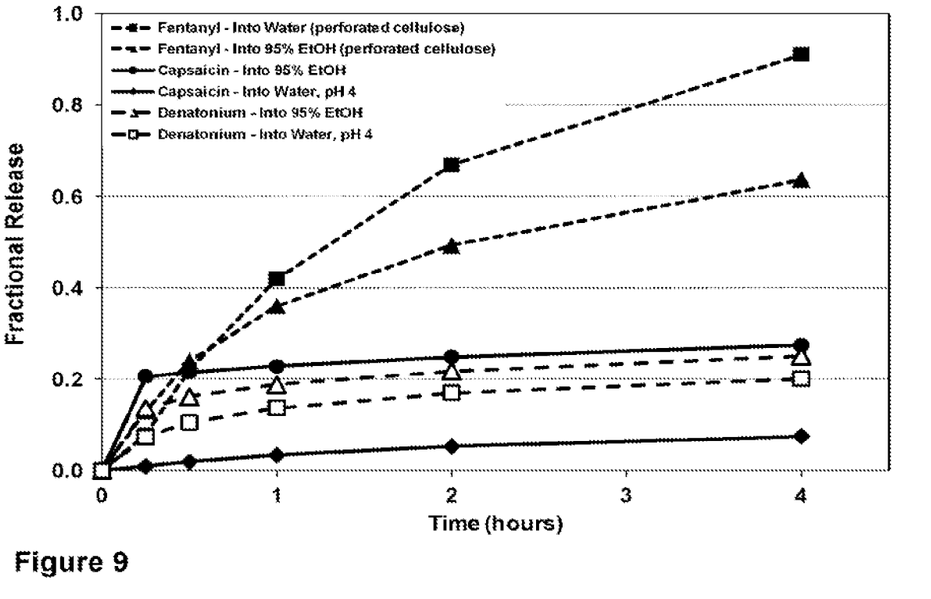
FIG. 9 is a representative graph of fractional release of aversive agents and fentanyl into water or 95% ethanol over time in the presence of perforated cellulose release liners.

Example 15. The release data obtained for fentanyl into 95% ethanol and into acidified water in the absence of a liner or in the presence of a perforated cellulose liner in Example 14 are combined with the capsaicin and denatonium release data obtained in Example 12. These combined graphs are shown for patches without a liner or with a perforated cellulose liner in FIG. 8 and FIG. 9, respectively. At least 70% of the aversive agent is still present in the patch after four hours wherein at least 60% of the fentanyl has been released.

What is claimed is:

1. An abuse deterrent or misuse deterrent transdermal patch system comprising:
   a patch backing layer comprising a distal side and a proximal side;
   one or more aversive agents incorporated onto the distal side of the backing layer; and
   an adhesive layer adhered to the proximal side of the backing layer comprising one or more therapeutically active agents,
   wherein the one or more aversive agents exhibits a biphasic release profile comprising an immediate release phase followed by an extended release phase when the transdermal patch system is immersed in a dissolution medium.

2. The system of claim 1, wherein the therapeutically active agent is selected from the group consisting of sex steroid hormones, non-steroidal anti-inflammatory agents, glucocorticoids, opioids, opiate analgesics, and stimulants.

3. The system of claim 1, wherein the one or more aversive agents is incorporated onto one or more polymeric thin film layers.

4. The system of claim 1, wherein the backing layer comprises one or more polyolefin, polyester, polyurethane, cellulose acetate, plasticized vinyl acetate-vinyl chloride copolymer, nylon, polyvinylidene chloride, ethylene-methacrylate copolymerer, aluminum foil or polymer-metal composite.

5. The system of claim 1, further comprising a release liner.

6. A method of reducing the potential abuse or misuse of a therapeutically active agent in a drug-containing patch system by an animal, comprising administering to the animal a patch system of claim 1.

7. The method of claim 6, wherein the animal is a human.

8. An abuse deterrent or misuse deterrent transdermal patch system comprising:
   a patch backing layer comprising a distal side and a proximal side;
   one or more aversive agents incorporated onto the distal side of the backing layer; and
   a permeable release liner.

9. The system of claim 8, further comprising an adhesive layer adhered to the proximal side of the backing layer.

10. The system of claim 9, wherein the transdermal patch system and the adhesive layer is free or essentially free of any drug.

11. The system of claim 9, wherein the adhesive layer comprises a therapeutically active agent.

12. The system of claim 11, wherein the therapeutically active agent is selected from the group consisting of sex steroid hormones, non-steroidal anti-inflammatory agents, glucocorticoids, opioids, opiate analgesics, and stimulants.

13. The system of claim 8, wherein the one or more aversive agents is incorporated onto one or more polymeric thin film layers.

14. The system of claim 8, wherein the backing layer comprises one or more polyolefin, polyester, polyurethane, cellulose acetate, plasticized vinyl acetate-vinyl chloride copolymer, nylon, polyvinylidene chloride, ethylene-methacrylate copolymerer, aluminum foil or polymer-metal composite.

15. The system of claim 8, wherein the release liner is laminated to the adhesive layer.

16. A method of reducing the potential abuse or misuse of a therapeutically active agent in a drug-containing patch system by an animal, comprising administering to the animal a patch system of claim 8.

17. The method of claim 16, wherein the animal is a human.

18. The system of claim 8, wherein the one or more aversive agents exhibits a biphasic release profile comprising an immediate release phase followed by an extended release phase when the transdermal patch system is immersed in a dissolution medium.

19. The system of claim 8, wherein the one or more aversive agents exhibits an immediate release phase when the transdermal patch system is immersed in a dissolution medium.

20. The system of claim 8, wherein the one or more aversive agents exhibits an extended release phase when the transdermal patch system is immersed in a dissolution medium.

21. The system of claim 8, wherein the one or more therapeutically active agents on the proximal side of the impermeable backing layer prevents delivery of the one or more therapeutically active agents to the distal side of the backing layer.

22. The system of claim 8, wherein the permeable release liner includes one or more perforations or openings.

23. The system of claim 5, wherein the release liner is permeable.

24. The system of claim 5, wherein the release liner includes one or more perforations or openings.

* * * * *